United States Patent [19]

Myers

[11] Patent Number: 6,019,605
[45] Date of Patent: Feb. 1, 2000

[54] METHOD FOR TREATING PERIODONTAL DISEASE

[76] Inventor: Terry D. Myers, 3701 Lakecrest Dr., Bloomfield Hills, Mich. 48304

[21] Appl. No.: 09/135,898

[22] Filed: Aug. 18, 1998

[51] Int. Cl.[7] .................................................. A61L 5/00
[52] U.S. Cl. ............................................................. 433/215
[58] Field of Search ................................................ 433/215

[56] References Cited

U.S. PATENT DOCUMENTS

| | | | |
|---|---|---|---|
| 4,877,401 | 10/1989 | Higuchi et al. | 433/215 |
| 5,055,048 | 10/1991 | Vassiliadis et al. | 433/215 |
| 5,090,908 | 2/1992 | Teumim-Stone | 433/215 |
| 5,342,198 | 8/1994 | Vassiliadis et al. | 433/215 |
| 5,435,724 | 7/1995 | Goodman et al. | 433/215 |
| 5,456,603 | 10/1995 | Kowalyk et al. | 433/215 |
| 5,642,997 | 7/1997 | Gregg, II et al. | 433/215 |
| 5,795,153 | 8/1998 | Rechmann | 433/215 |

OTHER PUBLICATIONS

"Practical Periodontics and Aesthetic Dentistry" vol. 9, No. 6, Aug. 1997.

*Primary Examiner*—John J. Wilson
*Assistant Examiner*—Patrick A. Hilsmier
*Attorney, Agent, or Firm*—Gifford, Krass, Groh, Sprinkle, Anderson & Citkowski, P.C.

[57] ABSTRACT

A method for treating periodontal disease in the periodontal pocket and for rendering the periodontal pocket resistant to future bacterial infection. After necrotic soft tissue and plaque is removed from the periodontal pocket by debridement, an optical fiber is inserted into the periodontal pocket. Laser emission is transmitted through the optical fiber into the periodontal pocket to substantially eradicate any remaining bacteria in the periodontal pocket and to also render the periodontal pocket resistant to subsequent bacterial infection. Optionally, the optical fiber is inserted into the periodontal pocket prior to debridement and laser radiation is transmitted through the optical fiber into the periodontal pocket and against both the soft and hard tissue. Such laser radiation not only kills bacteria in the periodontal pocket but also loosens the plaque which is typically present on the tooth and desensitizes the area surrounding the periodontal pocket.

17 Claims, 1 Drawing Sheet

METHOD FOR TREATING PERIODONTAL DISEASE

BACKGROUND OF THE INVENTION

I. Field of the Invention

The present invention relates generally to dental methods and, more particularly, to a dental method for treating periodontal disease.

II. Description of the Prior Art

It is well known that periodontal disease is caused by bacteria in the periodontal pocket. Such bacteria host not only in the soft tissue around the periodontal pocket, but also in plaque which is formed on the tooth. such bacteria not only cause swelling of the gums, pain and possible loss of the tooth, but can also render the patient more susceptible to other types of diseases, including heart disease.

In the conventional treatment of periodontal disease, instruments are inserted into the periodontal pocket to mechanically debride not only the plaque from the tooth but also remove the necrotic soft tissue by curettage. Antibiotics are also conventionally placed in the periodontal pocket following such conventional treatment for periodontal disease.

Even with conventional debridement and curettage of the periodontal pocket, it is well known that subsequent bacterial infections of the periodontal pocket following treatment are both commonplace and relatively rapid. This is particularly true since the patient may not exercise proper dental care following the treatment for the periodontal disease. Consequently, such subsequent bacterial reinfection of the periodontal pocket oftentimes necessitates further debridement of hard and soft tissue from the periodontal pocket.

SUMMARY OF THE PRESENT INVENTION

The present invention provides a method for treating periodontal disease in the periodontal pocket which renders the periodontal pocket resistant to subsequent bacterial infection.

In brief, in the method of the present invention, debridement of the plaque from the teeth as well as diseased soft tissue in the periodontal pocket is performed in the conventional fashion. Following such debridement, however, an optical fiber is inserted into the periodontal pocket and laser radiation is emitted through the optical fiber and against not only the soft tissue but also the plaque within the periodontal pocket. For reasons not entirely understood, such laser radiation of the periodontal pocket following debridement has been found to render the periodontal pocket resistant to subsequent bacterial reinfection of the periodontal pocket.

In the preferred method of the invention, an Nd:YAG pulse laser is used to emit the radiation into the periodontal pocket. Preferably, the laser is pulsed at a rate between 2 hertz and continuous wave and, more preferably, at a repetition rate of between 15 and 25 hertz. The energy of each pulse is preferably in the range of 80–120 millijoules per pulse and the laser radiation is continued for a period of 1–45 seconds up to a maximum power of about 2 watts per periodontal pocket.

Optionally, the optical fiber is inserted into the periodontal pocket prior to the debridement of plaque and soft tissue and the laser radiation is emitted into the periodontal pocket. Such initial laser radiation has been found not only to kill bacteria within the periodontal pocket, but to also loosen the plaque attached to the tooth. Such loosening of the plaque facilitates the manual debridement of the plaque from the tooth. Such laser radiation also desensitizes the area surrounding the periodontal pocket.

In order to enhance absorption of the laser radiation within the periodontal pocket, a dark pigment is also optionally inserted into the periodontal pocket and against both the plaque and diseased soft tissue prior to the step of applying the laser.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
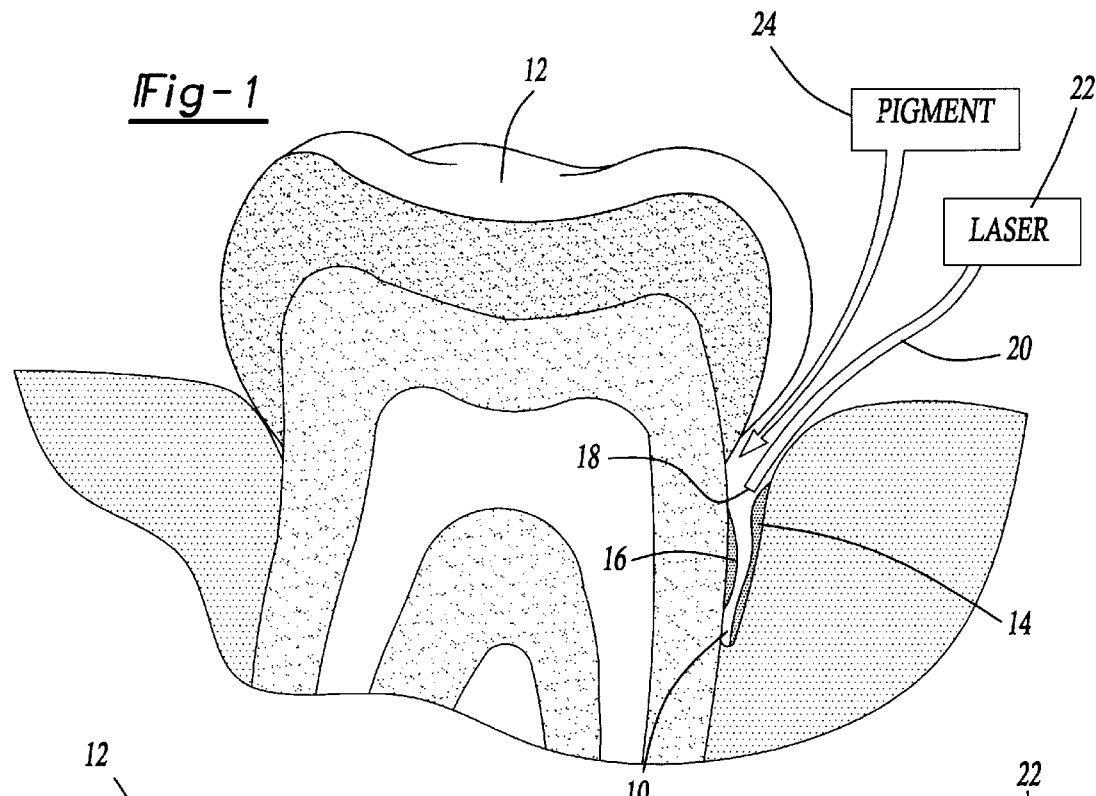
FIG. 1 is a diagrammatic view illustrating the laser radiation of a diseased periodontal pocket.

With reference first to FIG. 1, a periodontal pocket 10 next to a patient's tooth 12 is therein illustrated. The periodontal pocket 10 includes both diseased soft tissue 14 as well as plaque 16 attached to the tooth 12. Both the diseased soft tissue 14 and plaque 16 form hosts for bacteria of the type causing periodontal disease.

In order to treat the periodontal disease, a free end 18 of an optical fiber 20 is inserted into the periodontal pocket. The optical fiber preferably has a diameter of between 300 and 600 microns.

A laser 22 is optically connected to the other end of the optical fiber 20 so that, upon activation, the laser 22 emits laser radiation through the optical fiber 20 and against both the plaque 16 and diseased soft tissue 14 contained within the periodontal pocket. Preferably, the laser 22 is a Nd:YAG laser which emits radiation at a primary wavelength of 1064 nanometers.

The initial radiation of the laser 22 into the periodontal pocket 10 has been found not only to kill bacteria contained within the periodontal pocket 10, but also to loosen the plaque 16 attached to the tooth 12. The laser radiation of the periodontal pocket 10 also causes an analgesic effect for the patient and results in a numbing of the area surrounding the periodontal pocket. Such numbing renders the subsequent debridement of the plaque 16 and diseased soft tissue 14 less painful than without the laser radiation.

Preferably, the laser 22 is a pulsed laser having a repetition rate of between 2 hertz up to continuous wave and, more preferably, a repetition rate of between 15 hertz and 25 hertz. The laser power 22, furthermore, preferably has an energy of between 80 and 120 millijoules per pulse and the time of the laser radiation is selected as a function not only of the repetition rate and energy per pulse rate such that the total power emitted into a single periodontal pocket is 2 watts or less. Typically, the laser radiation occurs for a period of about 30 seconds for a periodontal pocket of 6 millimeters or less in depth and 45 seconds for a periodontal pocket greater than 6 millimeters.

In order to enhance the absorption of the laser energy by both the diseased soft tissue 14 as well as the plaque 16, a dark pigment 24 is injected into the periodontal pocket 10 prior to activation of the laser 22. Such pigment 24 has been found to enhance absorption of the laser energy even though the actual optical output from an Nd:YAG laser at 1064 nanometers is invisible.

Figure 2:
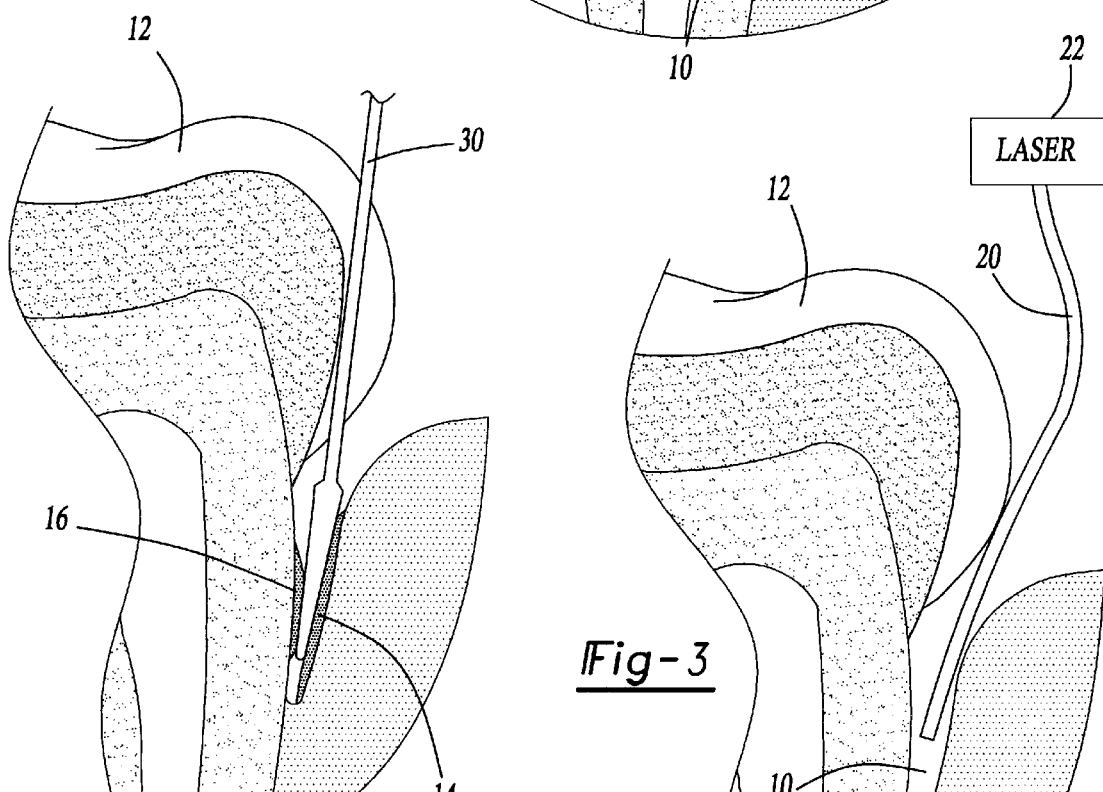
FIG. 2 is a diagrammatic view illustrating debridement and curettage of the periodontal pocket.

With reference now to FIG. 2, following the initial lasing step, conventional mechanical tools 30 are used to both remove the diseased necrotic tissue 14 by curettage as well as to debride the plaque 16 from the surface of the tooth 12. Such procedures are well known in dentistry and are known as root planing. As such, further description thereof is unnecessary.

Figure 3:
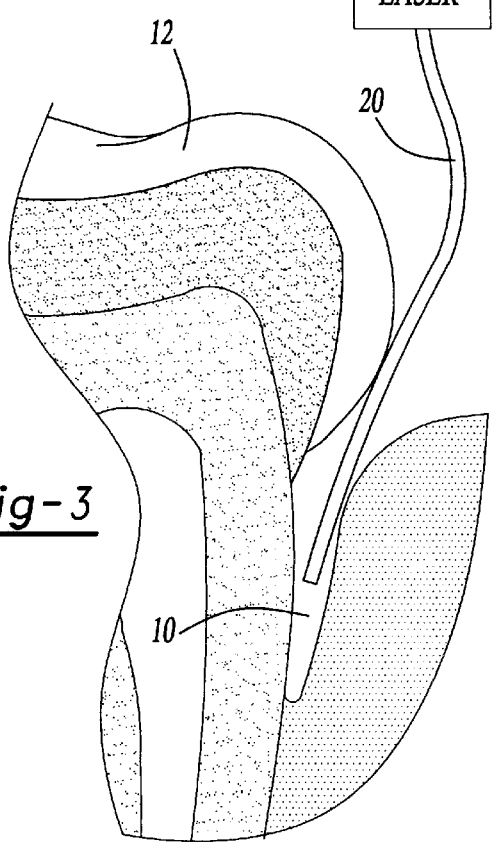
FIG. 3 is a diagrammatic view similar to FIG. 1, but illustrating the laser treatment of the periodontal pocket following debridement and curettage of the periodontal pocket.

With reference now to FIG. 3, following the debridement of the plaque 16 and diseased soft tissue 14 from the periodontal pocket 10, the optical fiber 20 is again reinserted into the periodontal pocket and the laser 22 is again activated. As before, the laser 22 is preferably a pulse Nd:YAG laser having a repetition rate of between 2 hertz and continuous wave and, more preferably, 15–25 hertz. Each pulse preferably has a width of approximately 150 microseconds and the power for each laser pulse is preferably in the range of 80–120 millijoules per pulse. The duration of the exposure ranges typically from 30–45 seconds such that the maximum power is less than 2 watts. As before, a pigment 24 can be injected into the periodontal pocket in order to enhance absorption of the laser energy.

In practice, it has been found that laser radiation of the periodontal pocket following debridement of the plaque and diseased soft tissue renders the periodontal pocket more resistant to subsequent bacterial reinfection than with the previously known debridement and antibiotic treatments for periodontal disease. The precise reason that the laser renders the periodontal pocket more resistant to subsequent bacterial reinfection is unknown.

Having described my invention, however, many modifications thereto will become apparent to those skilled in the art to which it pertains without deviation from the spirit of the invention as defined by the scope of the appended claims.

I claim:

1. A method for treating periodontal disease in a periodontal pocket and for rendering the periodontal pocket resistant to future bacterial infection comprising the steps of:

inserting an optical fiber into the periodontal pocket, emitting laser radiation through said optical fiber in an amount sufficient to both substantially eradicate bacteria in the periodontal pocket and also render the periodontal pocket resistant to subsequent bacterial infection, debriding of soft tissue and plaque in the periodontal pocket prior to said emitting step, inserting the optical fiber into the periodontal pocket, and an additional emitting step of emitting laser radiation through said optical fiber prior to said debriding step.

2. The invention as defined in claim 1 wherein said emitting step comprises the further steps of emitting pulsed radiation at a repetition rate of 2 hertz to a continuous pulse rate or a constant emission.

3. The invention as defined in claim 2 wherein said emitting step comprises the further steps of emitting pulsed laser radiation at an energy between 80 and 120 millijoules per pulse.

4. The invention as defined in claim 3 wherein said laser radiation comprises radiation from a Nd:YAG laser having a wavelength of substantially 1064 nanometers.

5. The invention as defined in claim 3 wherein said pulsed laser radiation has a total power of less than 2 watts.

6. The invention as defined in claim 2 wherein said pulsed radiation has a pulse width of substantially 150 microseconds.

7. The invention as defined in claim 1 wherein said emitting step further comprises the step of emitting laser radiation for 1–45 seconds.

8. The invention as defined in claim 1 and further comprising the step of applying a pigment to the periodontal pocket prior to said emitting step.

9. The invention as defined in claim 1 wherein said additional emitting step comprises the further step of emitting pulsed radiation at a repetition rate of 2 hertz to a continuous pulse rate or constant emission.

10. The invention as defined in claim 9 wherein said additional emitting step comprises the further step of emitting pulsed radiation at a repetition rate of 15 hertz–25 hertz.

11. The invention as defined in claim 9 wherein said additional step comprises the further step of emitting pulsed radiation at an energy between 80 and 120 millijoules per pulse.

12. The invention as defined in claim 9 wherein said pulse radiation has a pulse width during said additional emitting step is substantially 150 microseconds.

13. The invention as defined in claim 1 wherein during said additional emitting step said laser radiation during said additional emitting step comprises radiation from a Nd:YAG laser having a wavelength of substantially 1064 nanometers.

14. The invention as defined in claim 1 wherein during said additional emitting step, said laser radiation has a total power of less than 2 watts.

15. The invention as defined in claim 1 wherein said additional emitting step further comprises the step of emitting laser radiation for 1–45 seconds.

16. The invention as defined in claim 1 and further comprising the step of applying a pigment to the periodontal pocket prior to said additional emitting step.

17. The invention as defined in claim 1 wherein said emitting step further comprises the step of emitting radiation in an amount sufficient to desensitize the area surrounding the periodontal pocket.

* * * * *